United States Patent [19]

Myerowitz

[11] Patent Number: 5,475,095
[45] Date of Patent: Dec. 12, 1995

[54] NUCLEIC ACID COMPOSITIONS FOR THE ALPHA CHAIN OF BETA-HEXOSAMINIDASE

[75] Inventor: Rachel Myerowitz, Bethesda, Md.

[73] Assignee: The United States of America as represented by the Department of Health and Human Services, Washington, D.C.

[21] Appl. No.: 164,284

[22] Filed: Dec. 7, 1993

Related U.S. Application Data

[60] Continuation of Ser. No. 985,273, Dec. 3, 1992, abandoned, which is a division of Ser. No. 264,976, Oct. 31, 1988, Pat. No. 5,217,865, which is a continuation-in-part of Ser. No. 889,502, Jul. 25, 1986, abandoned.

[51] Int. Cl.$^6$ .............................. C07H 21/04; C12Q 1/68
[52] U.S. Cl. .................. 536/23.1; 435/6; 435/69.3; 435/91.2; 435/172.3; 435/810; 436/501; 436/22.1; 436/24.1; 436/24.3; 436/24.32; 436/24.33; 935/77; 935/78
[58] Field of Search .................. 435/6, 91.2, 810, 435/172.3, 69.3; 436/501; 536/22.1, 23.1, 24.1, 24.31–24.33; 935/77, 78, 88

[56] References Cited

U.S. PATENT DOCUMENTS 5,217,865  6/1993  Myerowitz ................................. 435/6

OTHER PUBLICATIONS

Myerowitz et al. (1985) Proc. Nat'l Acad Sci (USA) vol. 82, pp. 7830–7834.
Proia et al. (1987) the Journal of Biological Chemistry, vol. 262, No. 12, pp. 5677–5681.
Myerowitz et al. (1984) Proc. Nat'l Acad. Sci (USA), vol. 81, pp. 5394–5398.
Korneluk et al. (1986) the Journal of Biological Chemistry, vol. 261, No. 18, pp. 8407–8413.
Proia et al. (1982) Proc. Nat'l Acad. Sci (USA), vol. 79, pp. 6360–6364.

*Primary Examiner*—W. Gary Jones
*Assistant Examiner*—Ardin H. Marschel
*Attorney, Agent, or Firm*—Morgan & Finnegan

[57] ABSTRACT

Methods are disclosed of detecting mutations in the alpha chain gene that makes pre-natal diagnosis of Tay-Sachs disease possible. Screening for carrier heterozygotes of Tay-Sachs is made feasible by this invention.

8 Claims, 9 Drawing Sheets

```
-168        AGC CTC AGG TCC AGG CCG GAA GTG
        AAA GGG CAG GGT GTG GGT CCT CCT GGG
        GTC GCA GGC GCA GAG CCG CCT CTG GTC    -91

-90        ACG TGA TTC GCC GAT AAG TCA CGG GGG
        CGC CGC TCA CCT GAC CAG GGT CTC ACG
        TGG CCA GCC CCC TCC GAG AGG GGA GAC    -1
        CAG CGG GCC

1        ATG ACA AGC TCC AGG CTT TGG TTT TCG
   1        MET Thr Ser Ser Arg Leu Trp Phe Ser
            CTG CTG CTG GCG GCA GCG TTC GCA GGA
            Leu Leu Leu Ala Ala Ala Phe Ala Gly
            CGG GCG ACG GCC CTC TGG CCC TGG CCT
            Arg Ala Thr Ala Leu Trp Pro Trp Pro
            CAG AAC TTC                         90
            Gln Asn Phe                         30

91        CAA ACC TCC GAC CAG CGC TAC GTC CTT
  31        Gln Thr Ser Asp Gln Arg Tyr Val Leu
            TAC CCG AAC AAC TTT CAA TTC CAG TAC
            Tyr Pro Asn Asn Phe Gln Phe Gln Tyr
            GAT GTC AGC TCG GCC GCG CAG CCC GGC
            Asp Val Ser Ser Ala Ala Gln Pro Gly
            TGC TCA GTC                         180
            Cys Ser Val                         60

181        CTC GAC GAG GCC TTC CAG CGC TAT CGT
  61        Leu Asp Glu Ala Phe Gln Arg Tyr Arg
            GAC CTG CTT TTC GGT TCC GGG TCT TGG
            Asp Leu Leu Phe Gly Ser Gly Ser Trp
            CCC CGT CCT TAC CTC ACA GGG AAA CGG
            Pro Arg Pro Tyr Leu Thr Gly Lys Arg
            CAT ACA CTG                         270
            His Thr Leu                          90

271        GAG AAG AAT GTG TTG GTT GTC TCT GTA
  91        Glu Lys Asn Val Leu Val Val Ser Val
            GTC ACA CCT GGA TGT AAC CAG CTT CCT
            Val Thr Pro Gly Cys Asn Gln Leu Pro
            ACT TTG GAG TCA GTG GAG AAT TAT ACC
            Thr Leu Glu Ser Val Glu Asn Tyr Thr
            CTG ACC ATA                         360
            Leu Thr Ile                         120
```

FIG. 2B

```
361     AAT GAT GAC CAG TGT TTA CTC CTC TCT
121     Asn Asp Asp Gln Cys Leu Leu Leu Ser
        GAG ACT GTC TGG GGA GCT CTC CGA GGT
        Glu Thr Val Trp Gly Ala Leu Arg Gly
        CTG GAG ACT TTT AGC CAG CTT GTT TGG
        Leu Glu Thr Phe Ser Gln Leu Val Trp
        AAA TCT GCT                             450
        Lys Ser Ala                             150

451     GAG GGC ACA TTC TTT ATC AAC AAG ACT
151     Glu Gly Thr Phe Phe Ile Asn Lys Thr
        GAG ATT GAG GAC TTT CCC CGC TTT CCT
        Glu Ile Glu Asp Phe Pro Arg Phe Pro
        CAC CGG GGC TTG CTG TTG GAT ACA TCT
        His Arg Gly Leu Leu Leu Asp Thr Ser
        CGC CAT TAC                             540
        Arg His Tyr                             180

541     CTG CCA CTC TCT AGC ATC CTG GAC ACT
181     Leu Pro Leu Ser Ser Ile Leu Asp Thr
        CTG GAT GTC ATG GCG TAC AAT AAA TTG
        Leu Asp Val MET Ala Tyr Asn Lys Leu
        AAC GTG TTC CAC TGG CAT CTG GTA GAT
        Asn Val Phe His Trp His Leu Val Asp
        GAT CCT TCC                             630
        Asp Pro Ser                             210

631     TTC CCA TAT GAG AGC TTC ACT TTT CCA
211     Phe Pro Tyr Glu Ser Phe Thr Phe Pro
        GAG CTC ATG AGA AAG GGG TCC TAC AAC
        Glu Leu MET Arg Lys Gly Ser Tyr Asn
        CCT GTC ACC CAC ATC TAC ACA GCA CAG
        Pro Val Thr His Ile Tyr Thr Ala Gln
        GAT GTG AAG                             720
        Asp Val Lys                             240

721     GAG GTC ATT GAA TAC GCA CGG CTC CGG
241     Glu Val Ile Glu Tyr Ala Arg Leu Arg
        GGT ATC CGT GTG CTT GCA GAG TTT GAC
        Gly Ile Arg Val Leu Ala Glu Phe Asp
        ACT CCT GGC CAC ACT TTG TCC TGG GGA
        Thr Pro Gly His Thr Leu Ser Trp Gly
        CCA GGT ATC                             810
        Pro Gly Ile                             270
```

FIG. 2C

```
811        CCT GGA TTA CTG ACT CCT TGC TAC TCT
271        Pro Gly Leu Leu Thr Pro Cys Tyr Ser
           GGG TCT GAG CCC TCT GGC ACC TTT GGA
           Gly Ser Glu Pro Ser Gly Thr Phe Gly
           CCA GTG AAT CCC AGT CTC AAT AAT ACC
           Pro Val Asn Pro Ser Leu Asn Asn Thr
           TAT GAG TTC                                900
           Tyr Glu Phe                                300

901        ATG AGC ACA TTC TTC TTA GAA GTC AGC
301        MET Ser Thr Phe Phe Leu Glu Val Ser
           TCT GTC TTC CCA GAT TTT TAT CTT CAT
           Ser Val Phe Pro Asp Phe Tyr Leu His
           CTT GGA GGA GAT GAG GTT GAT TTC ACC
           Leu Gly Gly Asp Glu Val Asp Phe Thr
           TGC TGG AAG                                990
           Cys Trp Lys                                330

991        TCC AAC CCA GAG ATC CAG GAC TTT ATG
331        Ser Asn Pro Glu Ile Gln Asp Phe MET
           AGG AAG AAA GGC TTC GGT GAG GAC TTC
           Arg Lys Lys Gly Phe Gly Glu Asp Phe
           AAG CAG CTG GAG TCC TTC TAC ATC CAG
           Lys Gln Leu Glu Ser Phe Tyr Ile Gln
           ACG CTG CTG                                1080
           Thr Leu Leu                                 360

1081       GAC ATC GTC TCT TCT TAT GGC AAG GGC
361        Asp Ile Val Ser Ser Tyr Gly Lys Gly
           TAT GTG GTG TGG CAG GAG GTG TTT GAT
           Tyr Val Val Trp Gln Glu Val Phe Asp
           AAT AAA GTA AAG ATT CAG CCA GAC ACA
           Asn Lys Val Lys Ile Gln Pro Asp Thr
           ATC ATA CAG                                1170
           Ile Ile Gln                                390

1171       GTG TGG CGA GAG GAT ATT CCA GTG AAC
391        Val Trp Arg Glu Asp Ile Pro Val Asn
           TAT ATG AAG GAG CTG GAA CTG GTC ACC
           Tyr MET Lys Glu Leu Glu Leu Val Thr
           AAG GCC GGC TTC CGG GCC CTT CTC TCT
           Lys Ala Gly Phe Arg Ala Leu Leu Ser
           GCC CCC TGG                                1260
           Ala Pro Trp                                 420
```

FIG. 2D

```
1261    TAC CTG AAC CGT ATA TCC TAT GGC CCT
 421    Tyr Leu Asn Arg Ile Ser Tyr Gly Pro
        GAC TGG AAG GAT TTC TAC GTA GTG GAA
        Asp Trp Lys Asp Phe Tyr Val Val Glu
        CCC CTG GCA TTT GAA GGT ACC CCT GAG
        Pro Leu Ala Phe Glu Gly Thr Pro Glu
        CAG AAG GCT                                1350
        Gln Lys Ala                                 450

1351    CTG GTG ATT GGT GGA GAG GCT TGT ATG
 451    Leu Val Ile Gly Gly Glu Ala Cys MET
        TGG GGA GAA TAT GTG GAC AAC ACA AAC
        Trp Gly Glu Tyr Val Asp Asn Thr Asn
        CTG GTC CCC AGG CTC TGG CCC AGA GCA
        Leu Val Pro Arg Leu Trp Pro Arg Ala
        GGG GCT GTT                                1440
        Gly Ala Val                                 480

1441    GCC GAA AGG CTG TGG AGC AAC AAG TTG
 481    Ala Glu Arg Leu Trp Ser Asn Lys Leu
        ACA TCT GAC CTG ACA TTT GCC TAT GAA
        Thr Ser Asp Leu Thr Phe Ala Tyr Glu
        CGT TTG TCA CAC TTC CGC TGT GAG TTG
        Arg Leu Ser His Phe Arg Cys Glu Leu
        CTG AGG CGA                                1530
        Leu Arg Arg                                 510

1531    GGT GTC CAG GCC CAA CCC CTC AAT GTA
 511    Gly Val Gln Ala Gln Pro Leu Asn Val
        GGC TTC TGT GAG CAG GAG TTT GAA CAG
        Gly Phe Cys Glu Gln Glu Phe Glu Gln
        ACC TGA GCC CCA GGC ACC GAG GAG GGT
        Thr ***
        GCT GGC TGT                                1620
                                                    529

1621    AGG TGA ATG GTA GTG GAG CCA GGC TTC
        CAC TGC ATC CTG GCC AGG GGA CGG AGC
        CCC TTG CCT TCG TGC CCC TTG CCT GCG
        TGC CCC TGT                                1710
```

FIG. 2E

```
1711    GCT TGG AGA GAA AGG GGC CGG TGC TGG
        CGC TCG CAT TCA ATA AAG AGT AAT GTG
        GCA TTT TTC TAT[AAT AAA CAT GGA TTA
        CCT GTG TTT                              1800

1801    AAA AAA AAA AGT GTG AAT GGC GTT AGG
        GTA AGG GCA CAG CCA GGC TGG AGT CAG
        TGT CTG CCC CTG AGG TCT TTT AAG TTG
        AGG GCT GGG                              1890

1891    AAT GAA ACC TAT AGC CTT TGT GCT GTT
        CTG CCT TGC CTG TGA GCT ATG TCA CTC
        CCC TCC CAC TCC TGA CCA TAT TCC AGA
        CAC CTG CCC                              1980

1981    TAA TCC TCA GCC TGC TCA CTT CAC TTC
        TGC ATT ATA TCT CCA AGG CGT TGG TAT
        ATG GAA AAA GAT GTA GGG GCT TGG AGG
        TGT TCT GGA                              2070

2071    CAG TGG GGA GGG CTC CAG ACC CAA CCT
        GGT CAC AAA AGA GCC TCT CCC CCA TGC
        ATA CTC ATC CAC CTC CCT CCC CTA GAG
        CTA TTC TCC                              2160

2161    TTT GGG TTT CTT GCT GCT GCA ATT TTA
        TAC AAC CAT TAT TTA AAT ATT ATT AAA
        CAC ATA TTG TTC TCT]                     2229
```

NUCLEIC ACID COMPOSITIONS FOR THE ALPHA CHAIN OF BETA-HEXOSAMINIDASE

This is a continuation of U.S. application Ser. No. 07/985,273, filed Dec. 3, 1992, now abandoned which is a divisional of U.S. application Ser. No. 07/264,976, filed Oct. 31, 1988, now U.S. Pat. No. 5,217,865 which is a continuation-in-part of U.S. application Ser. No. 06/889,502, filed Jul. 25, 1986, now abandoned.

BACKGROUND OF THE INVENTION

1. Technical Field

The present invention is related to the isolation and characterization of a cDNA clone containing the entire coding sequence for the alpha chain of beta-hexosaminidase. More particularly, the present invention is related to a method for either prenatal diagnosing or adult screening for a genetic defect which is associated with Tay-Sachs disease.

2. Description of the Background Art

Tay-Sachs disease is an inherited disorder caused by mutation in the alpha-chain of beta-hexosaminidase A, a lysosomal enzyme composed of two polypeptides designated the alpha and beta chains (Stanbury et al., 1983, Metabolic Basis of Inherited Disease, p. 945; Sandhoff et al., 1984, Neuropediatrics 15 Suppl., 85–92). Deficiency of beta-hexosaminidase A results in storage of its major substrate, $GM_2$ ganglioside. Progressive accumulation of substrate leads to the characteristic neurodegenerative changes of Tay-Sachs disease patients. The disease is heterogeneous displaying a wide range of severity and age of onset. An early onset and fatal form of the disorder referred to as "classic" Tay-Sachs disease has a ten fold higher gene frequency among Ashkenazi Jews than the general population. A less publicized group having a carrier frequency equal to that of Ashkenazi Jews is a population of non-Jewish French Canadians located in Eastern Quebec (Anderman et al., 1977 Prog. Clin. Biol. Res. 18:161). In terms of age-of-onset, clinical course and biochemical parameters, French Canadian patients are indistinguishable from Ashkenazi patients (Hechtman et al., 1983 Clin. Gen. 24:206).

Beta-Hexosaminidase is a lysosomal enzyme composed of two polypeptide chains, alpha and beta, encoded on different chromosomes. Association of these polypeptides, a prerequisite for catalytic activity, results in three isozymes. Of these, only the A isozyme (aB) is able to hydrolyze all known beta-hexosaminidase substrates (beta-N-acetylglucosaminides and beta-N-acetylgalactosaminides, as well as 6-sulfated beta-N-acetylglucosaminides). The β isozyme (ββ) is unable to hydrolyze $GM_2$ ganglioside and the sulfated substrates, whereas the S isozyme (αα) has little catalytic activity except toward the sulfated compounds (Stanbury et al., 1983, Metabolic Basis of Inherited Disease, p. 945; Sandhoff et al., 1984, Neuropediatrics 15 Suppl., 85–92). Different specificities in substrate binding and hydrolysis have been recently proposed for the alpha and beta chains (Kytzia et al., J. Biol. Chem. 256:7568–7572, 1985).

The biosynthesis of beta-hexosaminidase follows that of a typical lysosomal enzyme (Hasilik et al., 1984, in Lysosomes in Biology and Pathology, 7:pp3–16). Synthesis occurs on membrane-bound polysomes and insertion into the endoplasmic reticulum is followed by cleavage of the signal sequence and glycosylation of the enzyme. In the Golgi apparatus, the lysosomal enzymes are selected from the melange of glycoproteins for phosphorylation of certain mannose residues to form the recognition marker for binding to phosphomannosyl receptor and subsequent transport to the lysosomes. Within the lysosome, beta-hexosaminidase undergoes proteolytic processing from precursor to mature form. Association of the alpha and beta chains occurs after phosphorylation and is therefore thought to take place in the Golgi apparatus (Proia et al, J. Biol. Chem. 259:3350–3354, 1984).

Mutations in the genes encoding the alpha or beta chain of beta-hexosaminidase result in Tay-Sachs or Sandhoff disease, respectively—genetic disorders displaying both clinical and biochemical heterogeneity (Sandhoff et al., 1984, Neuropediatrics 15 Suppl., 85–92). The best known of these is the classic late-infantile form of Tay-Sachs disease that occurs among Jews of Ashkenazi origin. A recent study reported the isolation of a clone containing a cDNA fragment for the alpha chain of human beta-hexosaminidase and a deficiency of mRNA in Ashkenazi Tay-Sachs fibroblasts (Myerowitz et al., 1984, PNAS, USA, 81:5394). However, the isolation and characterization of a cDNA clone containing the entire coding sequence of the alpha chain of human beta-hexosaminidase, has not heretofore been achieved.

In order to detect the many different kinds of mutations in human alpha-chain beta-hexosaminidase genes in individuals clinically displaying Tay-Sachs disease, one must have the entire, full length cDNA. If not, one would miss those mutations occuring in that part of the gene for which there is no cDNA. For example, the French-Canadian mutation occurs at the 5'-end of the gene which the prior cDNA clone (Myerowitz et al. PNAS, 1984 supra) did not have. Therefore, it is quite evident that the prior clone would have never made it possible to detect and elucidate the nature of Tay-Sachs mutation, for example, in the non-Jewish French-Canadian population.

SUMMARY OF INVENTION

It is an object of the invention to provide a cDNA clone carrying the entire coding sequence for the alpha chain of beta-hexosaminidase (hereinafter beta-HA).

This invention includes methods for detecting either the splice junction mutation or the insertion mutation for Tay-Sachs disease in the Ashkenazi Jewish population.

It is another object of the present invention to provide a kit and a method for detecting mutation for Tay-Sach's disease in humans.

BRIEF DESCRIPTION OF DRAWINGS

FIG. 2 shows nucleotide and deduced amino acid sequence of the alpha chain of human betahexosaminidase. The nucleotide sequence and derived primary alpha-chain structure are composites obtained, as shown in FIG. 1, from clones pβHα-1, -2, -3, and -5 and show the 5'-untranslated region, the entire alpha-chain protein sequence, and the 3'-untranslated region. The nucleotides are numbered in the 5' to 3' direction, starting with the A of the ATG codon that encodes the initiator methionine; negative numbers refer to the 5'-untranslated region. Amino acids are numbered so that residue 1 is the initiator methionine. The three possible N-linked glycosylation sites are boxed, and the termination codon is indicated by ***. The polyadenylylation signal in the 3'-untranslated region is underlined. The sequence of the 3' extension (nucleotides 1777–2229) present on a second mRNA encoding the alpha chain, obtained from clone pβHα-4, is shown in brackets;

FIG. 3 shows Southern blot analysis of normal, French Canadian Tay-Sachs and Ashkenazi Tay-Sachs DNA. Normal (IMR90) and Ashkenazi Tay-Sachs (GM 515, GM 2968) fibroblast cultures were obtained from the Human Genetic Cell Repository, Institute for Medical Research, Camden, N.J. The non-Jewish French Canadian Tay-Sachs cells (WG 107, WG 733) were obtained from the Repository for Human Mutant Cell Strains, Montreal, Canada. DNA was isolated from these cultures as well as from whole blood leukocytes of a normal non-Canadian Ashkenazi individual (D.B.) who was not a heterozygote carrier for Tay-Sachs disease following standard procedures well known in the art. Genomic DNA of normals and mutants (7 μg) was digested to completion with EcoRI, fractionated on a 1% agarose gel and transferred to GeneScreen Plus (New England Nuclear Corp.) in 10×SSC. Transferred DNA was then hybridized at 42° in the presence of formamide to the insert of pβHα-5, a cDNA clone that contains the entire coding sequence for the alpha-chain of human beta-hexosaminidase and that had been labeled with $^{32}$P to a specific activity of 2×10$^9$ (count/min per μg of DNA) by the random primer method, all such methods being well known in the art. Blots were washed as suggested by the manufacturer and exposed for 36 h to x-ray film using a Cronex Hi Plus intensifying screen.

FIG. 5 shows an assay for the exon 11 insertion defect in various α-chain genotypes. Genomic DNA samples were assayed for the insertion defect as described in Experimental Procedures IMR 90 (normal), S.W., (Ashkenazi normal), S.S. (Ashkenazi obligate heterozygote carrier), R.B. (Ashkenazi with classic Tay-Sachs), B.B. (Ashkenazi obligate heterozygote, father of R.B.), T.B. (Ashkenazi obligate heterozygote, mother of R.B.), GM2968 (Ashkenazi with classic Tay-Sachs), GM3052 (Ashkenazi obligate heterozygote, mother of GM2968), GM3051 (Ashkenazi obligate heterozygote, father of GM2968), GM515 (Ashkenazi with classic Tay-Sachs). Exposure was for 2 hours.

DETAILED DESCRIPTION OF INVENTION

The above and various other objects and advantages of the present invention are achieved by a clone of complementary DNA (cDNA) carrying coding sequence for the entire alpha chain of beta-HA.

It is noted that unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Materials. The adult human liver cDNA library was obtained from S. Orkin (Children's Hospital Medical Center, Boston, Mass. 02115). The simian virus 40-transformed human fibroblast cDNA library was obtained from H. Okayama (NIH, Bethesda, Md.). Radioisotopes and the Colony/Plaque Screen was obtained from New England Nuclear; HATF nitrocellulose filters was obtained from Millipore; NA-45 DEAE membranes was obtained from Schleicher & Schuell; oligo(dT) cellulose type 3 was obtained from Collaborative Research, Waltham, Mass.; restriction enzymes and T4 DNA ligase was obtained from Boehringer Mannheim; dideoxy- and deoxynucleotide triphosphates, M13 mp8, mp9, mp10, and mp11 cloning vectors were obtained from Pharmacia-PL Biochemicals.

Figure 1:
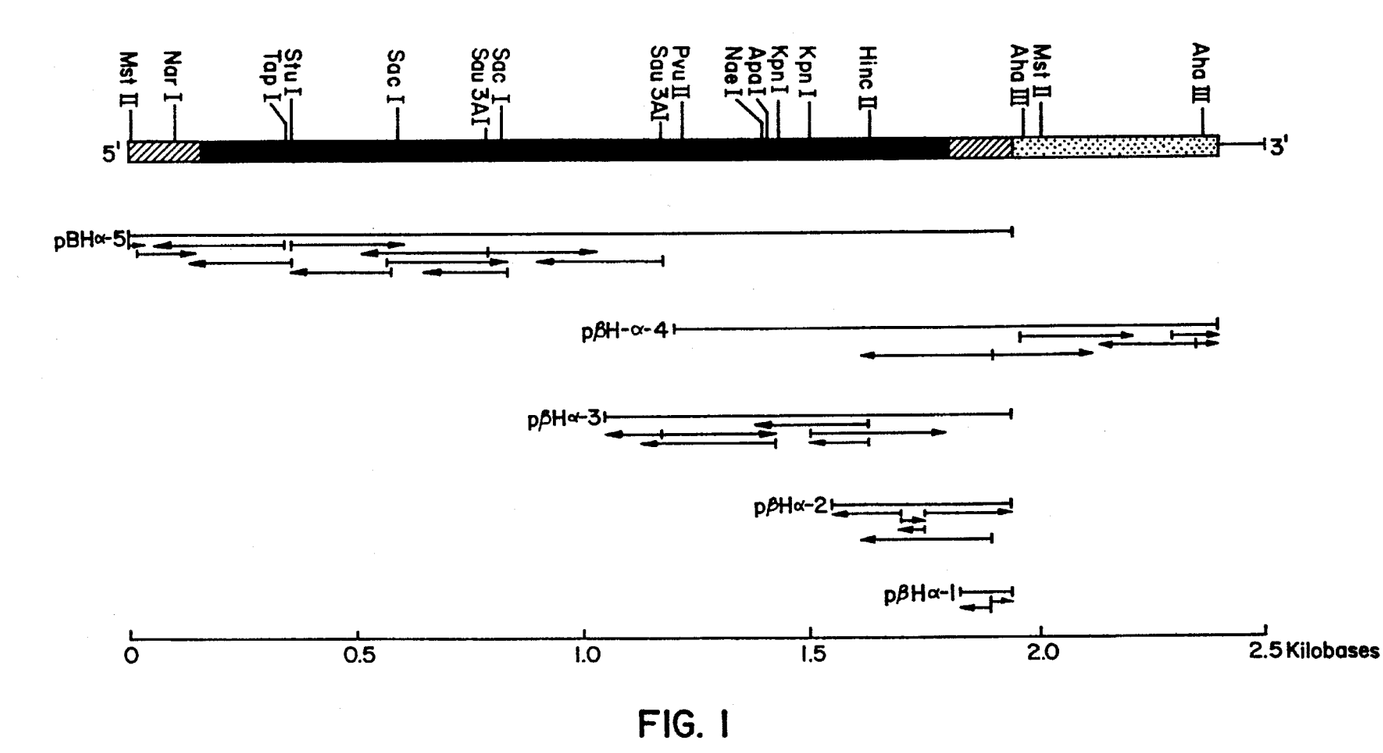
FIG. 1 represents the restriction map and sequencing strategy for obtaining the full sequence of cDNA for alpha-chain of beta-HA. The heavy black bar represents the coding region, the hatched bars designate the 5' and 3' untranslated regions, and the speckled bar represents the 3' extension present on a second mRNA encoding the alpha chain. The size [exclusive of poly(A) tail] and relationship of the cDNA inserts of pβHα-1, -2, -3, -4, and -5 are shown below the restriction map. The jagged line of pβHα-2 represents 37 bp coding for a region of an intron in the alpha-chain gene. Arrows below each cDNA insert show the direction and extent of DNA sequences.
Figure 2A:
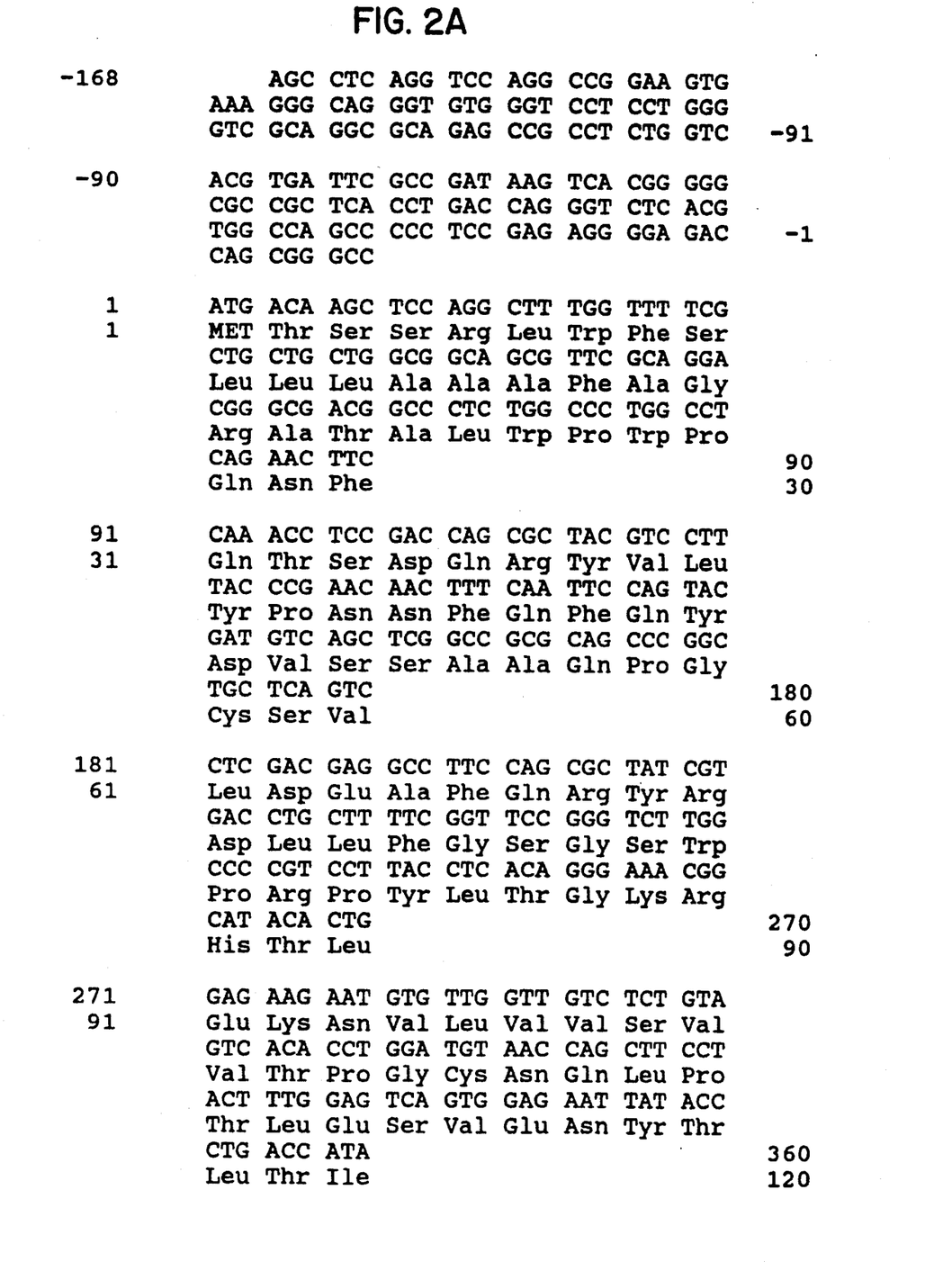
Figure 2B:
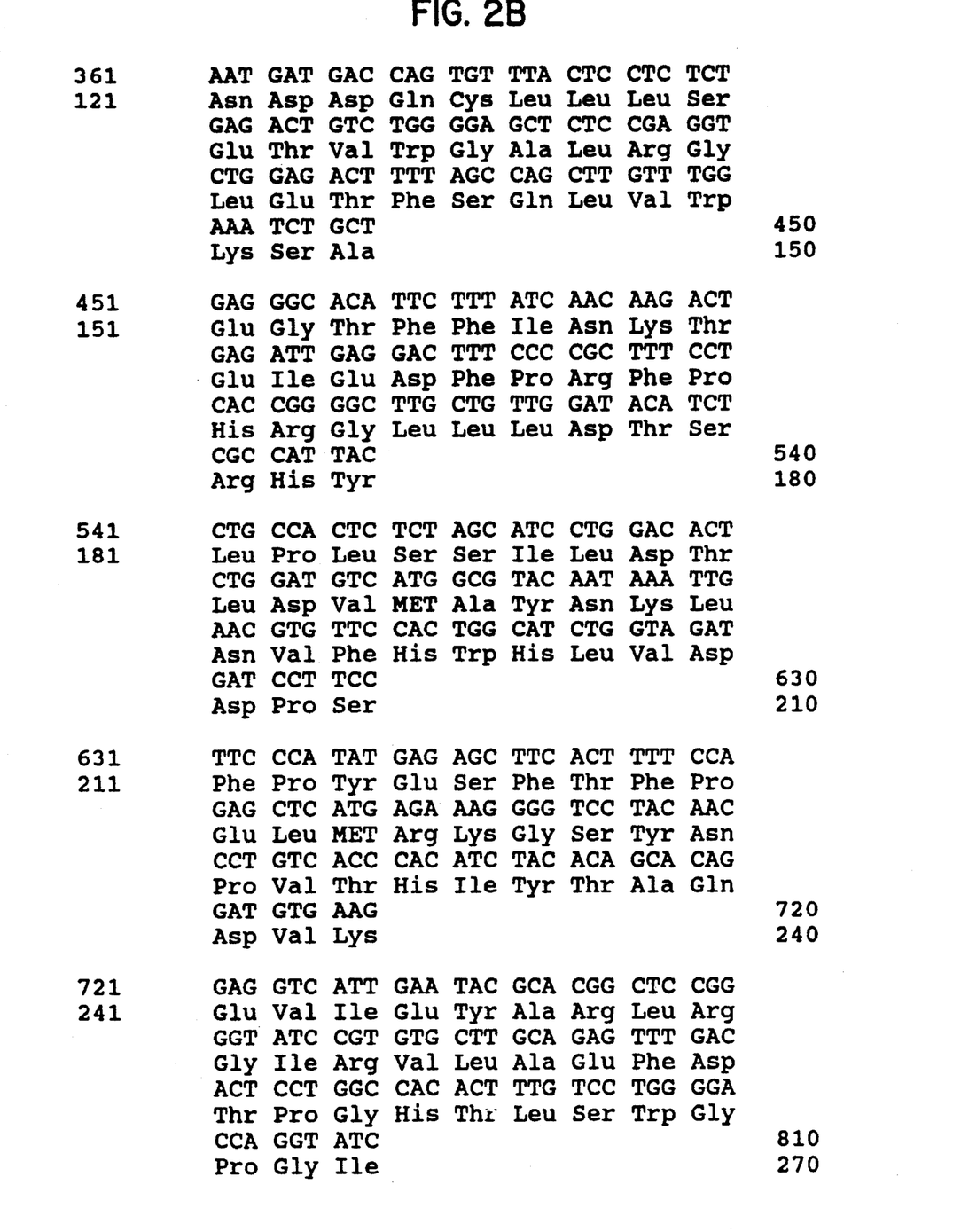
Figure 2C:
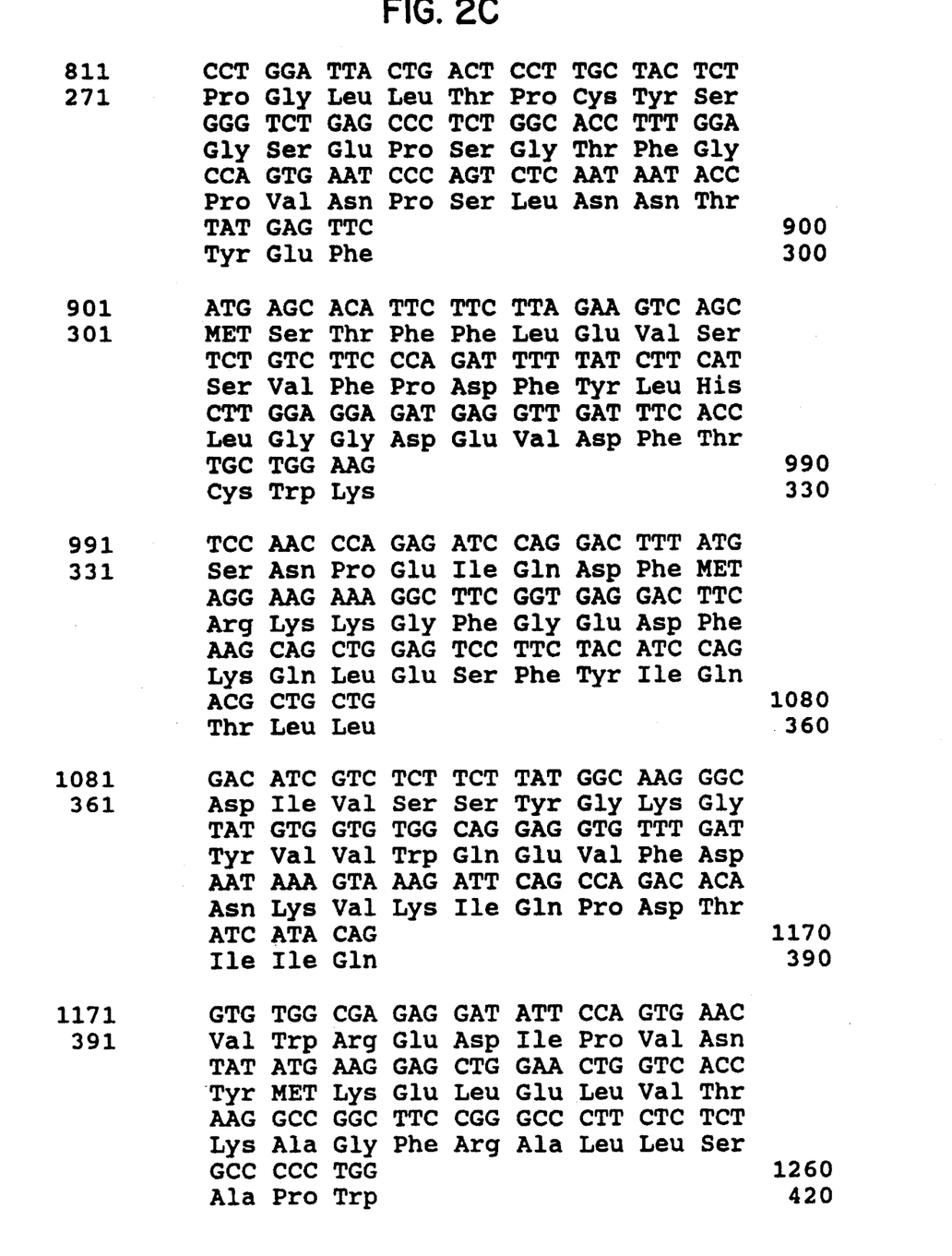
Figure 2D:
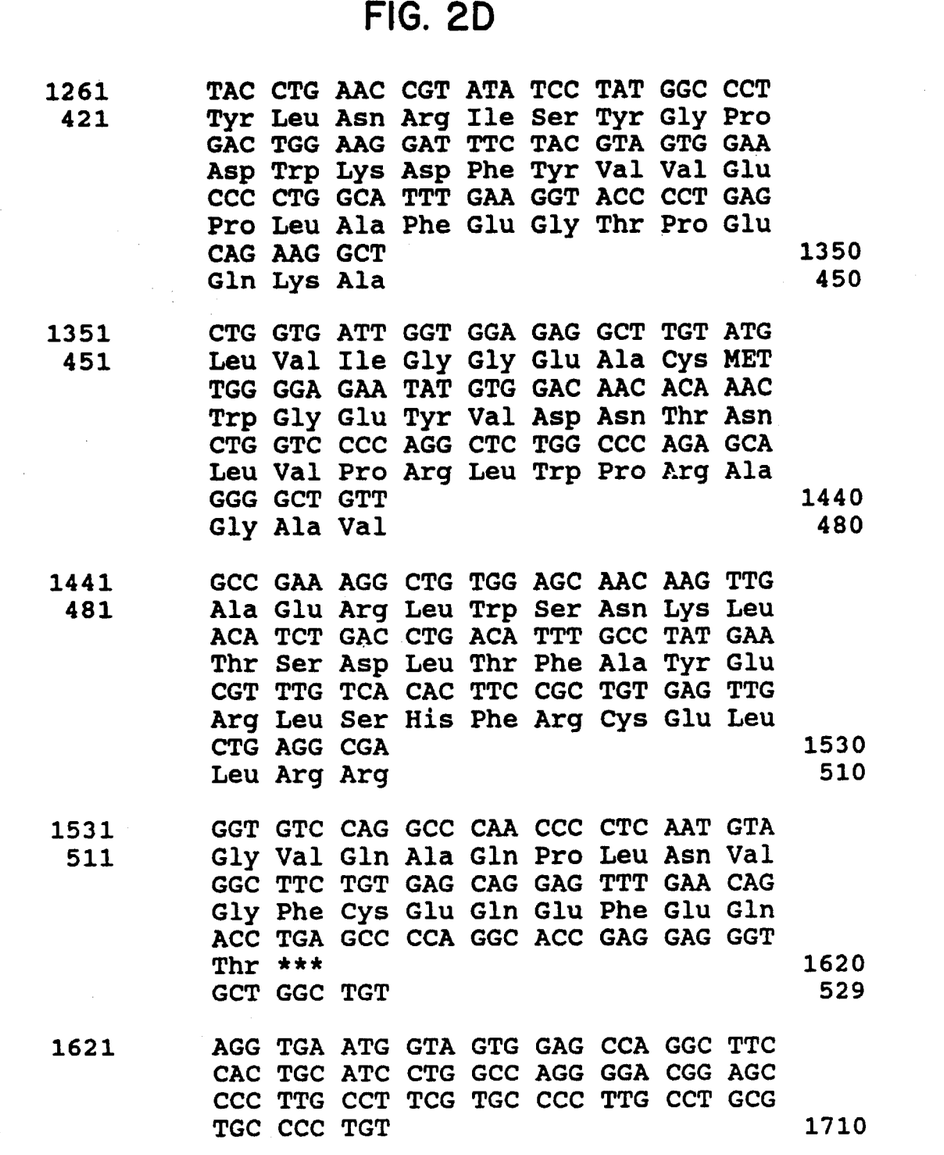
Figure 2E:
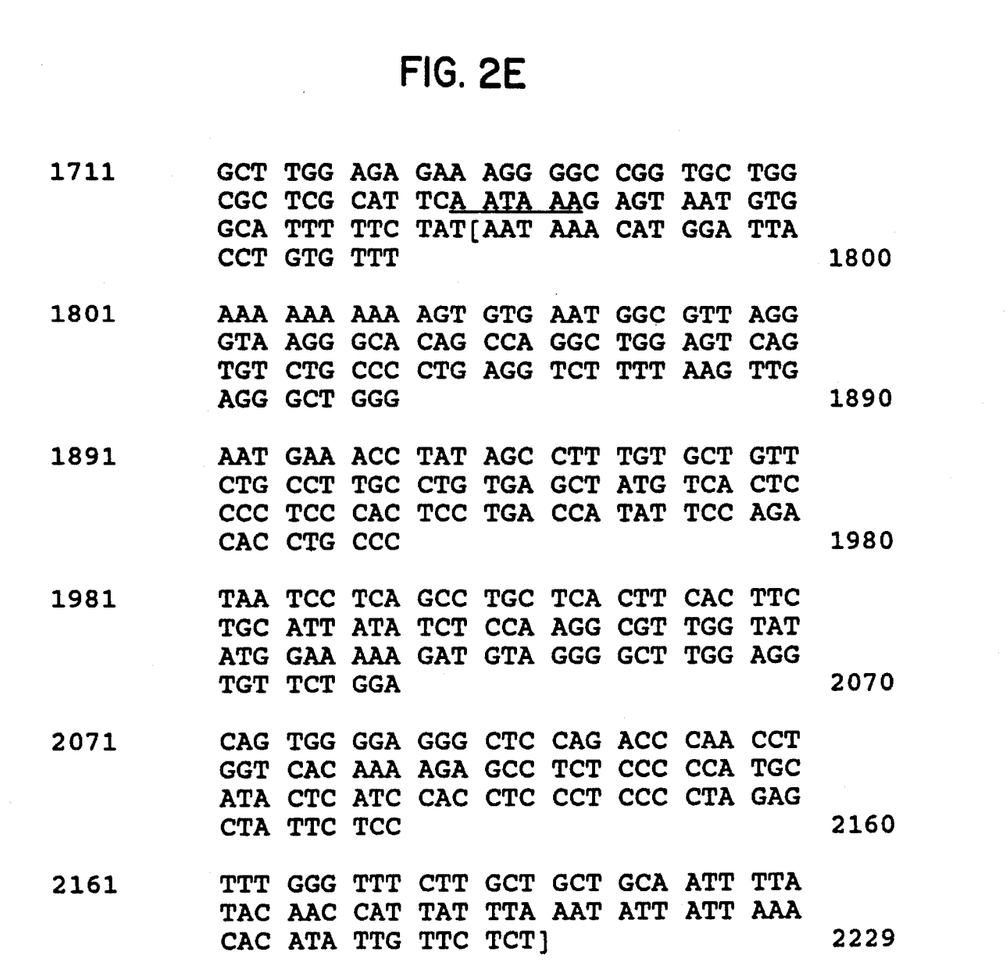

Isolation of cDNA Clones. The adult human liver library (Prochownik et al., 1983, J. Biol. Chem. 258:8389–8394) was plated at a density of 8000 colonies per 150-mm plate on HAFT Millipore filters. A set of replicas was grown and transferred to chloramphenicol-containing plates (200 μg/ml) to amplify the plasmids. The colonies were lysed and processed by the method described by Hanahan et al., 1980, (Gene 10:63–67) and then hybridized with $^{32}$P-labeled cDNA insert of pβHα-1 (2.5 ng/ml hybridization fluid) a cDNA insert encoding 119 base pairs (bp) of the 3' terminus of alpha-chain mRNA as described by Myerowitz et al 1984, supra. Three positive clones were obtained from 120,000 colonies screened. (Subsequent screenings of this and other libraries produced a similar frequency of positive clones.) These were rescreened at a density of 300 colonies per 100-mm plate. cDNA inserts were released from the vector by digestion with Pst I and their size was estimated by electrophoresis in a 1% agarose gel. Nucleotide sequence analysis of the longest clone, pβHα-2, showed it to contain a 393-bp cDNA insert with a 3'-terminal sequence identical to the sequence of pβHα-1 (FIG. 1). This insert was labeled with $^{32}$P and was used to screen a simian virus 40-transformed human fibroblast library (Okayama et al., 1983, Mol. Cell. Biol. 3:280–289). Screening of the library and analyses of the positive clones were similar to the procedure described above except that the library was plated on Colony/Plaque Screen and cDNA inserts were released from the vector by digestion with BamHI. The longest clone, pβHα-3, isolated from this screen contained an 891-bp alpha-chain cDNA insert (FIG. 1). To enhance the probability of finding clones encoding the 5' region of the alpha chain, a 300-bp fragment (Pst I/Apa I; FIG. 1) was isolated from the 5' terminus of pβHα-3 and used to reprobe the adult human liver library. Thus pβHα-5 (FIG. 1), a clone containing the entire coding sequence for the alpha chain of human beta-hexosaminidase, was obtained. The 3' end of the cDNA insert of pβHα-5 was found to be identical to pβHα-3 by restriction enzyme mapping.

A deposit of the cDNA containing the entire coding sequence for the complete alpha-chain of beta-HA has been made in the American Type Culture Collection, Bethesda, Md., under accession number 67161. Upon issuance of a patent, this deposit shall continue to be maintained for at least 30 years or for the life of the patent and made available to the public without restriction, of course, consistent with the provisions of the law in this regard.

DNA Sequence Analysis. The sequence analysis of cDNA fragments was carried out by the Sanger dideoxy chain-termination method (Sanger et al., 1977, Proc. Natl. Acad. Sci. USA 74:5463–5467) with appropriate M13 vectors, the 17-mer sequencing primer, and $^{35}$S-labeled dATP (Biggin et al., 1983, Proc. Natl. Acad. Sci. USA 80:3963–3965).

Cell Culture. Fibroblasts from a cystic fibrosis patient (GM 1348), from Ashkenazi Jewish Tay-Sachs disease patient (GM 515) (Human Genetic Cell Repository, Institute for Medical Research, Camden, N.J.), from a patient with Hurler syndrome (J.O.M.), and from non-Jewish French Canadian Tay-Sachs patients were grown as described by Sando et al., 1977, (Cell 12:619–627).

RNA Blot Hybridization. Poly(A)+ RNA from cultured human fibroblasts was electrophoresed in a 1% agarose/formaldehyde denaturing gel according to the procedure of Goldberg, 1980, (Proc. Natl. Acad. Sci. USA 77:5794–5798). Transfer of the RNA to Pall BIODYNE A transfer membrane (1.2 μm) (Pall, Glen Cove, N.Y.), hybridization with $^{32}$P-labeled probes, and washing of the blots were carried out as described by the manufacturer. Blots were exposed to Kodak x-ray film at −70° C. using a Cronex Hi Plus intensifying screen.

Chromosomal Localization. Isolation and characterization of human-mouse cell hybrids has been known (Shows et al., 1984, Somat. Cell Mol. Genet. 10:315–318). The human chromosome content of these hybrids was determined by karyotyping (Shows et al., 1978, Cytogenet. Cell Genet. 21:99–104) and enzyme marker analysis (Shows et al., 1983, Adv. Hum. Genet. 12:341–452). High molecular weight DNA prepared from mouse, human, and hybrid lines was digested with Pst I, and the resulting fragments were electrophoretically separated in a 1% agarose gel. DNA was transferred to nitrocellulose filters (Maniatis et al., 1982, Molecular Cloning: A Laboratory Manual). The filters were hybridized with $^{32}$P-labeled pβHα-2, washed, and exposed to the x-ray film as described (Maniatis, supra).

Computer Analysis. The nucleotide and amino acid sequences of the beta-hexosaminidase alpha chain and those of other lysosomal enzymes available in the literature were compared by the NUCLAN and PRTALN programs of Wilbur and Lipman (Proc. Natl. Acad. Sci. USA 80:726–730, 1983) and the significance of similarities was evaluated by the RDF program of Lipman and Pearson (Science 227:1435–1441, 1985).

Sequence Analysis of alpha-Chain cDNA Clones. The nucleotide sequence of the alpha-chain betahexosaminidase cDNA from the 5'-untranslated region to the poly(A) tail and the deduced amino acid sequence of the alpha-chain polypeptide are shown in FIG. 2. The cDNA is 1944 bp long, containing a 168-bp 5'-untranslated region with an in-frame termination codon found at nucleotide -85 to -87. A polyadenylylation signal (AATAAA) 22 bp upstream from the poly(A) tail punctuates the 186 bp 3'-untranslated region. A methionine-encoding triplet initiates an open reading frame of 1587 bp corresponding to 529 amino acids (Mr, 60,697) ending with a stop codon (nucleotides 1588–1590). The amino terminus is rich in hydrophobic residues characteristic of signal sequences. Three possible N-linked glycosylation sites are identified (nucleotides 343–345, 469–471, 883–885).

Figure 3:
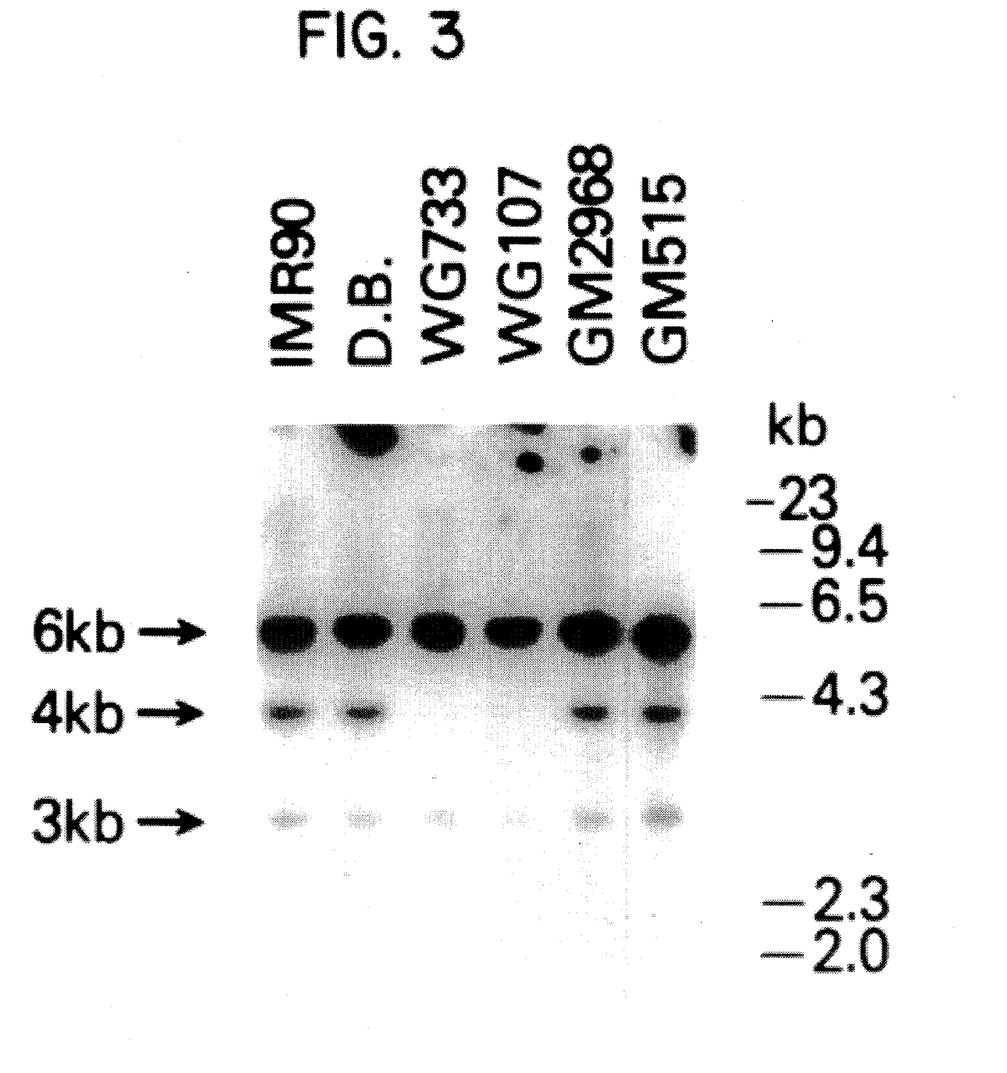

Results shown in FIG. 3 clearly establish that an identical restriction pattern is obtained for the normal controls and Ashkenazi Tay-Sachs samples comprising three DNA fragments with approximate sizes of 6, 4 and 3 kilobases (kb). However, the 4 kb DNA fragment was absent from the restriction pattern of the non-Jewish French Canadia Tay-Sachs samples. (A restriction pattern similar to normal controls was also observed with Ashkenazi samples digested with PstI, HindIII or KpnI.) These results indicate that the DNA from Ashkenazi patients did not show major alpha-chain gene alterations detectable by Southern blotting, while DNA from the Canadian patients displayed similar deletions of a portion of the alpha-chain gene.

The region deleted in the alpha-chain gene of the French Canadian Tay-Sachs samples was determined by analyzing a Southern blot of EcoRI digested normal and mutant DNA's which had been hybridized sequentially with 3' and 5' terminal alpha-chain cDNA probes prepared from pβHα-5. The 3' terminal cDNA probe (312 base pairs) hybridized to the 6 kb genomic DNA fragment in all of the samples identifying this fragment as the 3' end of the alpha-chain gene and demonstrating that the 3' end was intact in the French Canadian mutants. Rehybridization of this same blot with a 5' terminal alpha-chain probe (356 bp) elicited a band in the normal samples corresponding to the 4 kb DNA fragment, but failed to produce a signal in the French Canadian samples. These results mapped the 5' terminal of the alpha-chain gene to the 4 kb fragment in EcoRI digests and indicated that a 5' terminal region of this gene was deleted in French Canadian Tay-Sachs cell lines WG 107 and WG 733. This conclusion is supported by the results of an identical experiment performed with StuI digested normal and mutant DNA samples. Hybridization with the 5' terminal alpha chain cDNA probe failed to produce a signal in the mutants but did so in the normals, (0.6 kb), while the 3' terminal probe produced a signal (4.6 kb) in both types of DNA samples.

The size of the alpha-chain gene deletion in the French Canadian Tay-Sachs patients was estimated by hybridizing normal and mutant DNA with probes obtained from normal alpha-chain genomic clones. Following Southern transfer, normal and mutant DNAs that had been digested with EcoRI were hybridized with a $^{32}$P labeled genomic probe (300 bp). This probe mapped 700 bp upstream from the 5' end of the 5' terminal alpha-chain cDNA probe and hybridized with DNA in the normal samples but failed to hybridize with DNA in the French Canadian samples indicating that the mutants lack DNA sequences functioning in the initiation of alpha-chain gene transcription as well as 5' exonic piece(s) since the 5' terminal cDNA probe was obtained from a cDNA clone of full length or no more than 50–100 bp short.

Figure 4A:
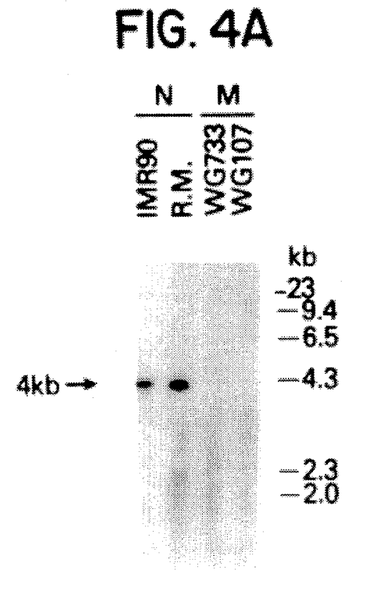
FIG. 4 shows the extent of the 5' terminal alpha-chain gene deletion in French Canadian Tay-Sachs Patients. Normal [IMR90, R.M. (an Ashkenazi Jewish non-Canadian subject who was not a heterozygote carrier for Tay-Sachs disease), D.B.] and French Canadian Tay-Sachs (WG 733, WG 107) DNA (10 μg/sample) was digested with EcoRI, fractionated on a 1% agarose gel, transferred to GeneScreen Plus and processed as described above except that the blots displayed in (B) and (C) were obtained by transfer in 0.4M NaOH and 0.6M NaCl. (A): Hybridization with a 300 bp DNA sequence obtained from an alpha-chain genomic clone and mapping 700 bp upstream from the 5' end of the 5' terminal cDNA probe. (B): Hybridization with a 600 bp alpha-chain intronic sequence obtained from an alpha-chain genomic clone and mapping 4.7 kb downstream from the 5' end of the 5' terminal alpha-chain cDNA probe. (C) Hybridization with a 300 bp alpha-chain intronic sequence obtained from an alpha-chain genomic clone and mapping 7.6 kb downstream from the 5' end of the 5' terminal cDNA probe. Exposure was for 48 hr. N=Normal and M=Mutant.
Figure 4B:
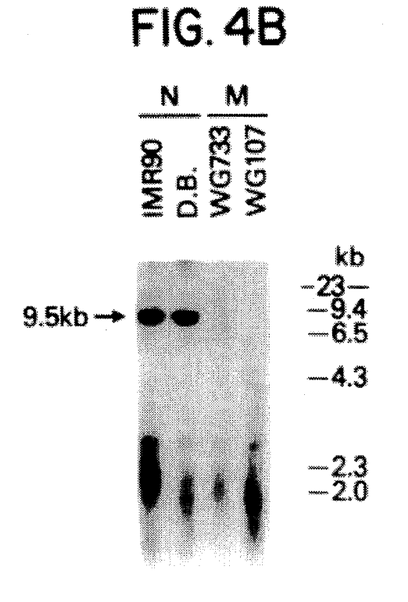
Figure 4C:
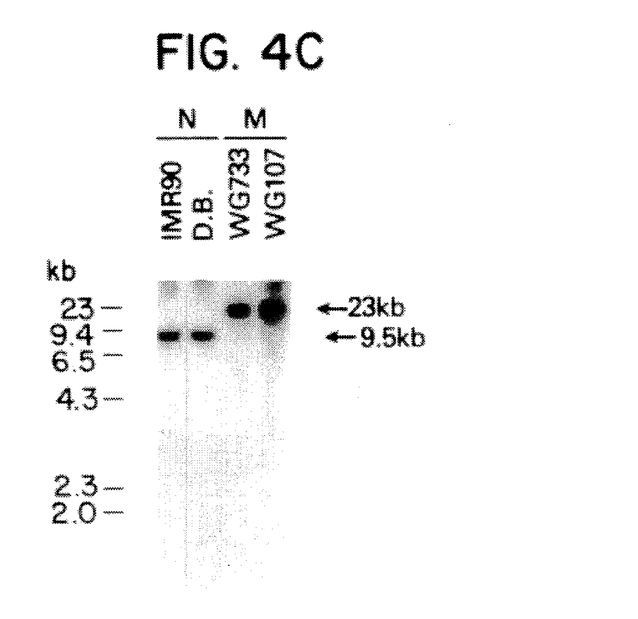
Figure 5:
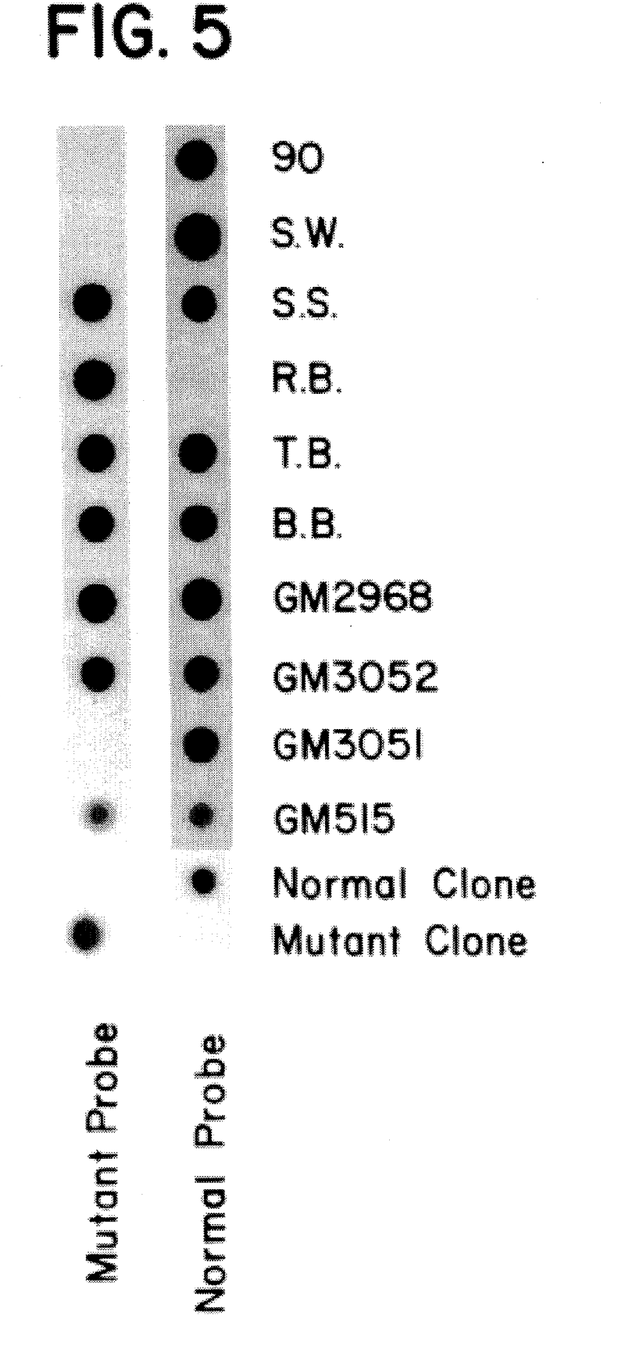

To delimit the 3' end of the deletion, normal and mutant DNA samples that had been digested with EcoRI and transferred to nylon-membranes were probed with two intronic protions of the α-chain gene. One intronic sequence (600 bp) mapping 4.7 kb downstream from the 5' end of the 5' terminal cDNA probe hybridized with the normal samples (9.5 kb band) but yielded no signal in the mutants (FIG. 3, B). A second intronic sequence (300 bp) mapping 7.6 kb downstream from the 5' end of the 5' terminal cDNA probe hybridized to both normal (a 9.5 kb band) and mutant (23 kb band) DNA samples (FIG. 4, C). (Hybridization of this probe to DNA fragments of different sizes in the normals and mutants results from alterations in the EcoRI restriction pattern of the mutant as a consequence of the deletion.) These results indicated that the α-chain deletion in French Canadian Tay-Sachs mutants extended between 5.3 and 7.6 kb downstream from the 5' terminus of the a-chain cDNA, assuming a minimum requirement of a 50 bp hybridization for production of a signal.

Apart from the general utility of the full length α-chain cDNA of the present invention in characterizing the mutations in the beta-HA encoding genes in individuals affected with Tay-Sachs disease the cDNA clone of the present invention can, also be readily used for prenatal diagnosis and heterozygote carrier screening of the French Canadian population which is a high risk group for this disorder. This is achieved as follows.

(a) First, isolate DNA from blood leucocytes of the person to be screened. In the case of a fetus isolate DNA from chronic villi. Include normal control DNA.

(b) Cleave the DNA with the restriction enzyme, such as EcoRI. In addition cleave DNA from a normal individual already determined not to be a Tay-Sachs carrier. Cleavage produces fragments of the genomic DNA of varying sizes.

(c) Electrophorese the cleaved λ DNA samples (patients and normals) on a 1% agarose gel. This separates the cleaved DNA (i.e. DNA fragments) by size. Include size standards (such as Hind III cleaved DNA) on the gel.

(d) After electrophoresis is complete, transfer the fractionated DNA fragments of the samples (normal and patients and standards) onto a nylon membrane by the method of Southern, which is referred herein as a Southern blot.

(e) Hybridize the Souther blot with a $^{32}$P (isotope) labeled 300 bp piece of DNA which has been obtained from the normal alpha-chain gene. This piece of DNA maps 7.3 kilobases downstream from the 3' end of the first exon of the alpha-chain normal gene, hence forth called the "intron probe". This intron probe hybridizes (binds) with the DNA fragment of the normal or patient EcoRI cleaved DNA on the Southern blot which contains base pairs complementary to it. After hybridization, wash the Southern blot as described herein supra, to remove nonspecifically bound isotope ($^{32}$P) and expose the blot to x-ray film following standard techniques well known in the art. Remove x-ray film after 24 hours and observe the radiograph. Results similar to FIG. 4, particularly FIG. 4(c) would be observed indicating the following:

1) Normal will give one band at 9.5 kilobases;

2) Heterozygote carrier will give 2 bands, one at 9.5 and the other at 23 kilobases.

3) An affected fetus or individual will give one band at 23 kilobases.

Similarly a diagnostic test for Tay-Sachs disease in the Ashkenazi Jewish population is prepared from the identified mutation as follows.

1) Isolate DNA from blood leukocytes of any Ashkenazi Jewish person to be screened. In case of a fetus, isolate DNA from chronic villi. Include normal control DNA.

2) Treat samples with an appropriate restriction enzyme and electrophorese on a 1% agarose gel. Transfer the fractionated DNA samples onto a nylon membrane according to the method of Southern (Southern blot). Make a duplicate blot of these samples.

3) Prepare a $^{32}$P labeled oligonucleotide probe (about 20 base pairs) which matches the sequence of the normal gene in the region of the mutation present in Ashkenazi Jewish Tay-Sachs patients (probe A). Prepare the same size probe which matches the analogous sequence in the mutant, that is matches the mutated base pair as well as the flanking regions (probe B).

4) Hybridize one Southern blot with probe A and the duplicate blot with probe B.

5) Results: Normal control DNA hybridized with probe A would form a stable hybrid and yield a signal whereas samples bearing the mutation would not yield a signal. This is due to the fact that a hybridization covering a short stretch of about 20 base pairs will be unstable with a single base pair mismatch.

6) Hybridization with probe B will yield the reverse results; the normal controls would form an unstable hybrid with this probe—that is no signal; but the mutants would.

7) Heterozygote carriers would form a stable hybrid with both probes.

A kit comprising a container containing the intact or fragmented cDNA of the present invention, either cryopreserved or otherwise, an oligonucleotide probe, an intron probe about 300 bp DNA and the like, including containers containing restriction enzymes and instructions to carry out the diagnostic and/or screening procedure as described herein is, of course, now made possible, conveniently put together and made available for clinical use in accordance with the present invention.

It is understood that the examples and embodiments described herein are for illustrative purposes only and that various modifications or changes in light thereof will be suggested to persons skilled in the art and are to be included within the spirit and purview of this application and the scope of the appended claims. The following examples use the methods and materials described above.

EXAMPLE 1

This example demonstrates a method for detecting a splice junction mutation for Tay-Sachs disease in the Ashkenazi Jewish population.

Genomic DNA isolated from cultured cells or blood was used (1 µg) as the template in the polymerase chain reaction to amplify a segment of DNA (117 bases) flanking the splice junction mutation. The reaction was carried out for 27 cycles utilizing two 23 base primers having the following sequences. PCA$_1$ has a sequence of 5'CCCCTGAGCA-GAAGGCTCTGGTG3'. PCA$_2$ has a sequence of 5'TCCT-GCTCTCAGGCCCAACCCTC3'.

These primers and Taq I polymerase along with a DNA amplification kit (sold by Gene Amp, Perkin Elmer Cetus) are used as described by the manufacturer's instructions with the exception that the unnealing step was performed at 55° C. Duplicate sets of samples (7-µl aliquots) were applied, denatured, and fixed to Biotrans membranes (0.2 µm) according to the DNA dot-blot protocol described by the manufacturer. Both sets of samples were prehybridized for 1 hour at 37° C. in 0.1% polyvinylpyrrolidone/0.1% Ficoll/0.1% bovine serum albumin/0.9M sodium chloride, 0.05M sodium phosphate, pH 8.3/0.005M EDTA/500 µg of denatured salmon sperm DNA per ml. One set of samples was hybridized with a $^{32}$P-labeled 19 base oligomer complementary to the sense strand of the normal allele (5' C-A-G-G-C-T-C-T-G-G-T-A-A-G-G-G-T-T-T 3'), and the other set was hybridized with a 19-base oligomer complementary to the send strand of the mutant allele (5'-C-A-G-G-C-T-C-T-G-C-T-A-A-G-G-G-T-T-T 3'). Filters were washed in 0.36M sodium chloride/0.02M sodium phosphate, pH 8.3/0.002M EDTA for 15 minutes at 4° C., then for 30 minutes at ambient temperature, and finally for 2 minutes at 53° C. The ambient-temperature wash solution was 0.1% in NaDodSO$_4$. Filters were exposed to x-ray film in the presence of a Cronex Hi Plus intensifying screen for 2 hours.

EXAMPLE 2

This example demonstrates a method for detecting an insertion mutation for Tay-Sachs disease in the Ashkenazi Jewish population.

Amplification of specific genomic DNA sequences is first conducted. Genomic DNA, isolated from either cultured cells, whole blood, or leukocyte pellets, was used (1 µg) as the initial template in the polymerase chain reaction to amplify a segment of exon 11 encompassing the insertion defect. The reaction was carried out for 27 cycles utilizing two 23 base primers, (5'-GTGTGGCGAGAGGATATTC-CAGT-3') and (5'-TTCAAATGCCAGGGGTTCCACTA-3').

A dot blot assay for the α-chain insertion defect is then conducted. One-twentieth of each amplified DNA sample was applied in duplicate to a Biotrans nylon membrane (0.2µ, ICN) denatured and fixed to the membrane according to the dot blot protocol supplied by the manufacturer. One set of samples was hybridized to mutant probe, (5'-GAAC-CGTATATCTATCCTA-3') with a sequence complementary to that found in mutant exon 11. The other set of samples was hybridized to normal probe, (5'-GAACCGTATATC-CTATGGC-3') with a sequence complementary to that found in normal exon 11. Both probes were end labeled to a specific activity of 5×10$^8$ cpm/µg with [γ-P$^{32}$] ATP (6000 Ci/mmole). The blots were washed and exposed to x-ray film at −70° C. in the presence of a Cronex intensifying screen.

I claim:

1. An isolated nucleic acid molecule encoding the entire alpha chain of beta-hexosaminidase having the DNA sequence recited in FIG. 2 selected from the group consisting of nucleotide residues -168 to 1776 and -168 to 2229.

2. An isolated nucleic acid molecule encoding the entire alpha chain of beta-hexosaminidase having the DNA sequence of beta-hexosaminidase DNA deposited under ATCC Accession Number 67161.

3. A DNA probe selected from the group consisting of:
5'-CAGGCTCTGGTAAGGGTTT-3';
5'-CAGGCTCTGCTAAGGGTTT-3';
5'-GAACCGTATATCTATCCTA-3'; and
5'-GAACCGTATATCCTATGGC-3'.

4. A DNA probe comprising the nucleic acid molecule of claim 1.

5. A DNA probe comprising the nucleic acid molecule of claim 2.

6. The DNA probe of claim 4 labeled with a detectable marker.

7. The DNA probe of claim 5 labeled with a detectable marker.

8. The DNA probe of claim 3 labeled with a detectable marker.

* * * * *